(12) United States Patent
Hochrainer

(10) Patent No.: US 7,793,655 B2
(45) Date of Patent: Sep. 14, 2010

(54) TWO-CHAMBER CARTRIDGE FOR PROPELLANT-FREE METERING AEROSOLS

(75) Inventor: Dieter Hochrainer, Bingen am Rhein (DE)

(73) Assignee: Boehringer Ingelheim Pharma GmbH & Co. KG, Ingelheim am Rhein (DE)

( * ) Notice: Subject to any disclaimer, the term of this patent is extended or adjusted under 35 U.S.C. 154(b) by 0 days.

(21) Appl. No.: 11/178,689

(22) Filed: Jul. 11, 2005

(65) Prior Publication Data

US 2005/0241635 A1   Nov. 3, 2005

Related U.S. Application Data

(63) Continuation of application No. 10/638,458, filed on Aug. 11, 2003, now abandoned, which is a continuation of application No. 09/805,818, filed on Mar. 14, 2001, now abandoned, which is a continuation of application No. 09/171,471, filed on Nov. 16, 1998, now abandoned.

(30) Foreign Application Priority Data

Apr. 19, 1996   (DE) ................. 196 15 422
Apr. 18, 1997   (WO) .............. PCT/EP97/01958

(51) Int. Cl.
  *A61M 11/00* (2006.01)
  *A61M 15/00* (2006.01)
  *A61M 16/10* (2006.01)
  *A61M 37/00* (2006.01)
  *B05D 7/14* (2006.01)

(52) U.S. Cl. ............. 128/200.14; 128/200.23; 128/203.12; 128/203.15; 128/203.19; 128/203.21; 604/86; 604/87; 604/88; 604/89; 604/90; 604/91; 604/92

(58) Field of Classification Search ............ 128/200.14, 128/200.23, 203.12, 203.15, 203.19, 203.21; 604/86–89, 415, 416, 92, 90, 91; 366/130; 206/219, 222, 221; 222/82, 83, 80, 129; 220/258.3, 258.4, 258.5, 200
See application file for complete search history.

(56) References Cited

U.S. PATENT DOCUMENTS 440,316 A   11/1890   Long (Continued)

FOREIGN PATENT DOCUMENTS

AU   230997   5/1959

(Continued)

*Primary Examiner*—Patricia M Bianco
*Assistant Examiner*—Nihir Patel
(74) *Attorney, Agent, or Firm*—Michael P. Morris; Mary-Ellen M. Devlin

(57) ABSTRACT

A cartridge for propellant-free administration of a liquid pharmaceutical composition by inhalation includes: an elongate displacing device including an upper end and a lower end, the lower end for at least partial insertion into a container; a cartridge chamber disposed at the lower end of the displacing device and operable store a pharmaceutical formulation, the cartridge chamber including at least one pierceably sealed opening; and a cannula guide extending from the upper end of the displacing device to the cartridge chamber, wherein insertion of a cannula through the guide pierces the sealed opening and releases the pharmaceutical formulation into a liquid solvent in the container to form the liquid pharmaceutical composition.

10 Claims, 4 Drawing Sheets

U.S. PATENT DOCUMENTS

| | | |
|---|---|---|
| 1,694,851 A | 12/1928 | Glass |
| 2,342,215 A | 2/1944 | Perelson |
| 2,362,103 A | 11/1944 | Smith |
| 2,424,801 A | 7/1947 | Crabbe et al. |
| 2,568,029 A | 9/1951 | Seemar |
| 2,629,421 A | 2/1953 | Ayres |
| 2,669,370 A | 2/1954 | Royal, Jr. |
| 2,793,776 A | 5/1957 | Lipari |
| 2,990,079 A | 6/1961 | Garvey |
| 3,172,568 A | 3/1965 | Moddema |
| 3,193,993 A | 7/1965 | Barton et al. |
| 3,198,194 A | 8/1965 | Wilburn |
| 3,255,972 A | 6/1966 | Hultgren et al. |
| 3,354,883 A | 11/1967 | Southerland |
| 3,355,238 A | 11/1967 | Schwartzman |
| 3,425,598 A | 2/1969 | Kobemick |
| 3,441,177 A | 4/1969 | Trehame, Jr |
| 3,625,403 A | 12/1971 | Rousselot |
| 3,648,899 A | 3/1972 | Lukesch et al. |
| 3,644,096 A | 4/1972 | Easter |
| 3,655,096 A | 4/1972 | Easter |
| 3,674,028 A | 7/1972 | Ogle |
| 3,715,189 A | 2/1973 | Nighohossian et al. |
| 3,842,836 A | 10/1974 | Ogle |
| 3,857,392 A | 12/1974 | Ogle |
| 3,858,580 A | 1/1975 | Ogle |
| 3,870,147 A | 3/1975 | Orth |
| 3,874,380 A | 4/1975 | Baum |
| 3,874,381 A | 4/1975 | Baum |
| 3,878,977 A | 4/1975 | Carlisle |
| 3,924,741 A | 12/1975 | Kachur et al. |
| 3,946,732 A | 3/1976 | Hurscham |
| 3,949,751 A | 4/1976 | Birch et al. |
| 4,008,820 A | 2/1977 | Ruetz |
| 4,019,512 A | 4/1977 | Tenczar |
| 4,045,860 A | 9/1977 | Winckler |
| 4,088,246 A | 5/1978 | Klingaman |
| 4,089,432 A | 5/1978 | Crankshaw et al. |
| 4,116,336 A | 9/1978 | Sorensen et al. |
| 4,162,030 A | 7/1979 | Capra et al. |
| 4,177,938 A | 12/1979 | Brina |
| 4,187,893 A | 2/1980 | Bujan |
| 4,195,730 A | 4/1980 | Hunt |
| 4,201,316 A | 5/1980 | Klingaman |
| 4,202,334 A | 5/1980 | Elson |
| 4,204,606 A | 5/1980 | Micheli |
| 4,264,018 A | 4/1981 | Warren |
| 4,315,570 A | 2/1982 | Silver et al. |
| 4,322,020 A | 3/1982 | Stone |
| 4,440,316 A | 4/1984 | Christine |
| 4,457,454 A | 7/1984 | Meshberg |
| 4,457,455 A | 7/1984 | Meshberg |
| 4,469,250 A | 9/1984 | Evezich |
| 4,479,989 A | 10/1984 | Mahal |
| 4,515,586 A | 5/1985 | Mendenhall et al. |
| 4,516,967 A | 5/1985 | Kopfer |
| 4,526,823 A | 7/1985 | Farrell et al. |
| 4,559,052 A | 12/1985 | Babson |
| 4,619,651 A | 10/1986 | Kopfer et al. |
| 4,637,934 A | 1/1987 | White |
| 4,638,927 A | 1/1987 | Morane |
| 4,676,775 A | 6/1987 | Zolnierczyk et al. |
| 4,727,985 A | 3/1988 | McNeirney et al. |
| 4,732,299 A | 3/1988 | Hoyt |
| 4,781,679 A | 11/1988 | Larkin |
| 4,799,599 A | 1/1989 | Herrmann |
| 4,817,830 A | 4/1989 | Yavorsky |
| 4,821,923 A * | 4/1989 | Skorka ................. 222/80 |
| 4,883,641 A | 11/1989 | Wicks et al. |
| 4,886,177 A | 12/1989 | Foster |
| 4,979,941 A | 12/1990 | Ogle, II |
| 4,982,875 A | 1/1991 | Pozzi et al. |
| 5,004,123 A | 4/1991 | Stoody |
| 5,024,087 A | 6/1991 | Nagasaki et al. |
| 5,031,384 A | 7/1991 | Rebeyrolle et al. |
| 5,038,958 A | 8/1991 | Dreier |
| 5,084,042 A | 1/1992 | McPhee |
| 5,102,010 A | 4/1992 | Osgar et al. |
| 5,105,995 A | 4/1992 | Martin |
| 5,129,894 A | 7/1992 | Sommermeyer et al. |
| 5,137,175 A | 8/1992 | Kowalski et al. |
| 5,158,810 A | 10/1992 | Oishi et al. |
| 5,176,178 A | 1/1993 | Schurter et al. |
| 5,188,628 A | 2/1993 | Rani et al. |
| 5,213,227 A | 5/1993 | Koyama et al. |
| 5,242,085 A | 9/1993 | Richter et al. |
| 5,246,142 A | 9/1993 | DiPalma et al. |
| 5,273,189 A | 12/1993 | Jouillat et al. |
| 5,289,818 A | 3/1994 | Citterio et al. |
| 5,292,033 A | 3/1994 | Gueret |
| 5,316,135 A | 5/1994 | Kneer et al. |
| 5,316,221 A | 5/1994 | Glover et al. |
| 5,325,977 A | 7/1994 | Haynes et al. |
| 5,331,121 A | 7/1994 | Tsuji |
| 5,332,113 A | 7/1994 | Kusler, III et al. |
| 5,332,121 A | 7/1994 | Schmidt et al. |
| 5,347,999 A | 9/1994 | Poss et al. |
| 5,352,196 A | 10/1994 | Haber et al. |
| 5,355,872 A | 10/1994 | Riggs et al. |
| 5,370,272 A | 12/1994 | Gueret |
| 5,385,251 A | 1/1995 | Dunn |
| 5,395,365 A | 3/1995 | Weiler et al. |
| 5,421,485 A | 6/1995 | Furuta et al. |
| 5,455,124 A | 10/1995 | Schollenberger |
| 5,480,067 A | 1/1996 | Sedlmeier |
| 5,487,739 A | 1/1996 | Aebischer et al. |
| 5,497,909 A | 3/1996 | Wirsig et al. |
| 5,497,944 A | 3/1996 | Weston et al. |
| 5,507,409 A | 4/1996 | Paradine |
| 5,509,564 A | 4/1996 | Knoop |
| 5,509,578 A | 4/1996 | Livingstone |
| 5,511,558 A | 4/1996 | Shepard et al. |
| 5,514,123 A | 5/1996 | Adolf et al. |
| 5,520,972 A | 5/1996 | Ezaki et al. |
| 5,520,975 A | 5/1996 | Inoue et al. |
| 5,533,994 A | 7/1996 | Meyer |
| 5,569,191 A | 10/1996 | Meyer |
| 5,579,760 A | 12/1996 | Kohler |
| 5,620,434 A | 4/1997 | Brony |
| 5,642,838 A | 7/1997 | Stoody |
| 5,657,910 A | 8/1997 | Keyser |
| 5,672,321 A | 9/1997 | Daykin |
| 5,730,328 A | 3/1998 | Maeder et al. |
| 5,738,670 A | 4/1998 | Grippi |
| 5,752,629 A | 5/1998 | Hardy |
| 5,772,080 A | 6/1998 | de Pous et al. |
| 5,782,345 A | 7/1998 | Guasch et al. |
| 5,813,570 A | 9/1998 | Fuchs et al. |
| 5,827,262 A | 10/1998 | Nefftel et al. |
| 5,833,088 A | 11/1998 | Kladders et al. |
| 5,873,491 A | 2/1999 | Garcia et al. |
| 5,875,936 A | 3/1999 | Turbett et al. |
| 5,878,915 A | 3/1999 | Gordon et al. |
| 5,893,484 A | 4/1999 | Fuchs et al. |
| 5,894,841 A | 4/1999 | Voges |
| 5,910,138 A | 6/1999 | Sperko et al. |
| 5,934,510 A | 8/1999 | Anderson |
| 5,935,101 A | 8/1999 | Kato et al. |
| 5,944,217 A | 8/1999 | Baena |
| 5,968,619 A | 10/1999 | Carmen et al. |
| 6,013,363 A | 1/2000 | Takahashi et al. |
| 6,041,969 A | 3/2000 | Parise |
| 6,062,213 A | 5/2000 | Fuisz et al. |
| 6,062,430 A | 5/2000 | Fuchs |

| | | | | | | |
|---|---|---|---|---|---|---|
| 6,073,807 | A | 6/2000 | Wilford et al. | EP | 0654419 | 5/1995 |
| 6,109,315 | A | 8/2000 | Stern | EP | 0 661 218 | 7/1995 |
| 6,129,236 | A | 10/2000 | Osokin et al. | EP | 0763482 | 3/1997 |
| 6,152,296 | A | 11/2000 | Shih | EP | 0 812 625 A2 | 12/1997 |
| 6,223,746 | B1 | 5/2001 | Jewett et al. | EP | 0629165 | 7/1998 |
| 6,223,933 | B1 | 5/2001 | Hochrainer et al. | EP | 0972723 A2 | 1/2000 |
| 6,244,472 | B1 | 6/2001 | Hennemann | FR | 780 143 | 4/1935 |
| 6,280,431 | B1 | 8/2001 | Domkowski et al. | FR | 780143 | 4/1935 |
| 6,286,700 | B1 | 9/2001 | Davidson | FR | 1.112.540 | 3/1956 |
| 6,364,163 | B1 | 4/2002 | Mueller | FR | 1112540 | 3/1956 |
| 6,390,332 | B2 | 5/2002 | Wakayama | FR | 1159909 | 7/1958 |
| 6,481,435 | B2 | 11/2002 | Hochrainer et al. | GB | 854163 | 11/1960 |
| 6,481,535 | B1 | 11/2002 | Hochrainer et al. | IT | 449648 | 6/1949 |
| 6,598,762 | B2 | 7/2003 | McKune | IT | 449648 | 12/1949 |
| 6,742,677 | B2 | 6/2004 | Petit et al. | JP | 01-195858 | 8/1989 |
| 6,986,346 | B2 | 1/2006 | Hochrainer et al. | JP | 1195858 | 8/1989 |
| 7,040,311 | B2 | 5/2006 | Hochrainer et al. | JP | 09225356 A | 9/1997 |
| 2001/0009151 | A1 | 7/2001 | Hochrainer | JP | 64-034367 | 2/1998 |
| 2002/0007155 | A1 | 1/2002 | Freund et al. | WO | WO 90/06267 | 6/1990 |
| 2008/0033391 | A1 * | 2/2008 | Hochrainer ............... 604/416 | WO | WO 90/07319 | 7/1990 |

FOREIGN PATENT DOCUMENTS

| | | | | | |
|---|---|---|---|---|---|
| | | | WO | WO 91/14468 | 10/1991 |
| | | | WO | WO92/16439 | 10/1992 |
| AU | 4552085 | 1/1986 | WO | WO 93/23165 | 11/1993 |
| CA | 2251828 | 10/1997 | WO | WO 943373 | 2/1994 |
| DE | 442671 | 4/1927 | WO | WO 95/15895 | 6/1995 |
| DE | 28 47 929 | 5/1980 | WO | PCT US95/09384 | 2/1996 |
| DE | 3446697 | 6/1986 | WO | WO 96/03218 | 2/1996 |
| EP | 0 114 964 A1 | 8/1984 | WO | WO 96/03344 A1 | 2/1996 |
| EP | 0169501 | 1/1986 | WO | WO9701329 | 1/1997 |
| EP | 0 182 094 A2 | 5/1986 | WO | WO 97/06842 | 2/1997 |
| EP | 0 217 425 | 4/1987 | WO | WO 97/12687 | 4/1997 |
| EP | 0 315 440 B1 | 4/1989 | WO | WO97/18143 | 5/1997 |
| EP | 0322980 | 7/1989 | WO | WO 97/26998 | 7/1997 |
| EP | 0 368 112 | 5/1990 | WO | WO97/39831 | 10/1997 |
| EP | 0 495 330 A1 | 7/1992 | WO | WO9827959 | 7/1998 |
| EP | 0532873 A1 | 3/1993 | WO | WO 9848943 | 11/1998 |
| EP | 0577200 A1 | 1/1994 | WO | WO99/43571 | 9/1999 |
| EP | 0 622 311 | 2/1994 | WO | WO 0049988 | 3/2000 |
| EP | 0 585 908 A2 | 3/1994 | WO | WO 00/27543 | 5/2000 |
| EP | 0 621 027 A1 | 10/1994 | WO | WO 00/49988 | 8/2000 |
| EP | 0635254 | 1/1995 | | | |
| EP | 0653359 | 5/1995 | * cited by examiner | | |

TWO-CHAMBER CARTRIDGE FOR PROPELLANT-FREE METERING AEROSOLS

CROSS REFERENCE TO RELATED APPLICATIONS

This application claims priority to and is a continuation of: U.S. patent application Ser. No. 10/638,458, filed Aug. 11, 2003, now abandoned, which is a continuation of U.S. patent application Ser. No. 09/805,818, filed Mar. 14, 2001, now abandoned, which is a continuation of U.S. patent application Ser. No. 09/171,471, filed Nov. 16, 1998, now abandoned.

BACKGROUND OF THE INVENTION

1. Field of the Invention

The present invention relates to a two-chamber cartridge for liquids, particularly for drug formulations for use in propellant-free metering aerosols.

2. Description of Related Art

International Patent Application WO91/14468 "Atomizing Device and Methods" describes a device for propellant-free administration of a metered quantity of a liquid pharmaceutical composition for use by inhalation. A further developed embodiment is described, for example, in PCT/EP96/04351. For applications of this kind it is required to package the solutions containing the active substance into containers in such a way as to include only tiny residues of air and gas. Gas bubbles would lead to uncertainty in the accurate metering of the active substance. Containers of this kind are disclosed for example in International Patent Application PCT/EP95/03183. The containers described therein are particularly suitable for those pharmaceutical compositions which can be stored for lengthy periods in the form of an aqueous or ethanolic solution. For active substances which decompose in their solutions after only a few months there have not hitherto been any suitable containers which would allow commercial use of such sensitive preparations in propellant-free metering aerosols.

BRIEF SUMMARY OF THE INVENTION

The invention now relates to a cartridge which has two chambers for separate storage of active substance and solvent. The cartridge is constructed so that, when the cartridge is inserted in a device for producing the aerosol, the chamber containing the active substance is pierced by means of a cannula, with the result that the active substance comes into contact with the solvent and is dissolved. The storage time of the pharmaceutical preparation can be extended significantly by the separate storage of active substance and solvent. The active substance may be present in the chamber as a powder, granules or in the form of a tablet. Similarly, pharmacologically acceptable excipients may be present. Generally, those galenic formulations which ensure ease of solution of the active substance in the solvent are preferred. In the case of tablets, excipients which bring about better dissolution of the tablet may be added. Similarly excipients may be added which increase the stability of the active substances. In many cases, the active substance may also be present in the chamber in dissolved form if the active substance is stable in the solvent and the solvent is miscible with the solvent in the other chamber, hereinafter also referred to as container.

BRIEF DESCRIPTION OF THE DRAWINGS

The invention is hereinafter explained in more detail with reference to some specific embodiments by way of example.

FIG. 1 shows an axial section along the longitudinal axis of the cartridge (1) in accordance with the invention with the chamber (2) for receiving the active substance, the chamber (2) being an integral part of the closure cap (3)

FIG. 2 shows another embodiment of the closure cap (3) with chamber (2) when the cartridge is in its closed state, the container (4) being merely indicated.

FIGS. 3*a* to 3*c* show further embodiments of the closure cap (3) in accordance with the invention with chamber (2).

FIG. 4 shows a section along the longitudinal axis of an embodiment of the closure cap in accordance with the invention, in which the chamber (2) contains a minitablet (16*a*) as its supply of active substance.

DETAILED DESCRIPTION OF THE DRAWINGS

FIG. 1 shows the cartridge (1) in accordance with the invention consisting of a container (4) and a closure cap (3). The closure cap has a device (5)—in this case in the form of an immersed connector—through which some of the contents of the container (4) are displaced during the closure process and the container is filled with virtually no air bubbles. An internal encircling bead (6) on the lower edge of the closure cap (3) engages underneath a cylindrical ring (7) running around the outside of the neck of the container in the closed position. In the closed position the gap between the flat part of the closure cap (3) and the upper edge of the neck of the container, which may optionally have an encircling rib (10) to improve the seal, is filled by a sealing ring (11) and in this way the interior of the container (3) is sealed off. The internal diameter of the sealing ring (11) is appropriately such that it fits tightly against the connector (5). The vent opening or opening(s) (8) may also be located at other points on the outside of the cap, e.g. on the side in the cylindrical part of the cap.

In another embodiment (FIG. 2*a*) the closure cap (3) is closed off by a sleeve (20) made of aluminum which is crimped in position. The sleeve (20) is constructed so as to have a central opening (21) for the insertion of the cannula (22). This opening may be closed off by a septum as a protection against dust and other contaminants. This closure technique is known, for example, in injection ampoules.

In one particular embodiment the container (4) contains a collapsible internal container (4*a*) of flexible material. The internal container may, in a preferred embodiment, be fixed to the lower part of the container (4) by a device (12).

The chamber (2) is located in the lower part of the connector (5), the chamber being closed off to the outside by means of a partition, e.g. in the form of a septum (13), and to the interior of the container (4*b*) by means of a partition, e.g. in the form of a film (14). The septum (13) and film (14) are made from a material which can easily be pierced by a cannula having a pointed or rounded tip. The septum (13) is preferably made of a material which seals the interior (4*b*) off to the outside even when the cannula has pierced it. Usually, the partitions consist of thin plastics or aluminum foil. In one embodiment the septum (13) may have frangible points where it is connected to the side wall of the connector (5), so that when the partition is pierced it tears open at the frangible points. Preferably, the film (14) is in the form of a welded-on diffusion-tight sealing film which tears when pierced and allows the active substance to enter the interior (4*b*) of the container. The frangible points may also be provided in the region of the lower side wall of the connector (5) so that the lower part of the side wall of the connector is also torn away.

The position of the partition (13) may vary within wide areas of the interior of the connector (5), but it is preferably arranged in accordance with the quantity of active substance (16) so that the interior formed by the two partitions (13) and (14) contains, in addition to the powder, the least possible amount of gas (air).

FIG. 2 also shows an axial section through the neck of a container with a closure cap (3) fitted thereon, the chamber (2) being of different configuration.

FIG. 3a shows another embodiment of the closure cap according to the invention, in which the interior of the immersed connector is constructed so as to form a guide (17) for a cannula for drawing off liquid. In the present instance, the vent openings (8) are provided in the upper part of the container (4). As already described, the vent openings may alternatively be provided on the closure cap. The chamber (2) for holding the active substance is arranged separately in the lower part of the connector (5). Instead of a pierceable partition (14), frangible points (18) may be provided so that, as the partition (13) is pierced the chamber is torn away at the frangible points (18) by pressure on the partition (14). In this embodiment, the partition (14) may be constructed as the base of the connector (5).

FIG. 3b shows an embodiment in which the guide (17) merges into a press fit (19). The press fit is designed, in terms of diameter and length, so that on the one hand the resistance for pushing the cannula through is kept to a minimum and, on the other hand, a sufficient seal is achieved between the connector and the cannula.

FIG. 3c shows an embodiment with an elastic O-ring seal (20) between the connector and the piercing cannula (not shown in the drawing). The device which prevents the O-ring from accidentally becoming detached is not shown.

Figure 1:
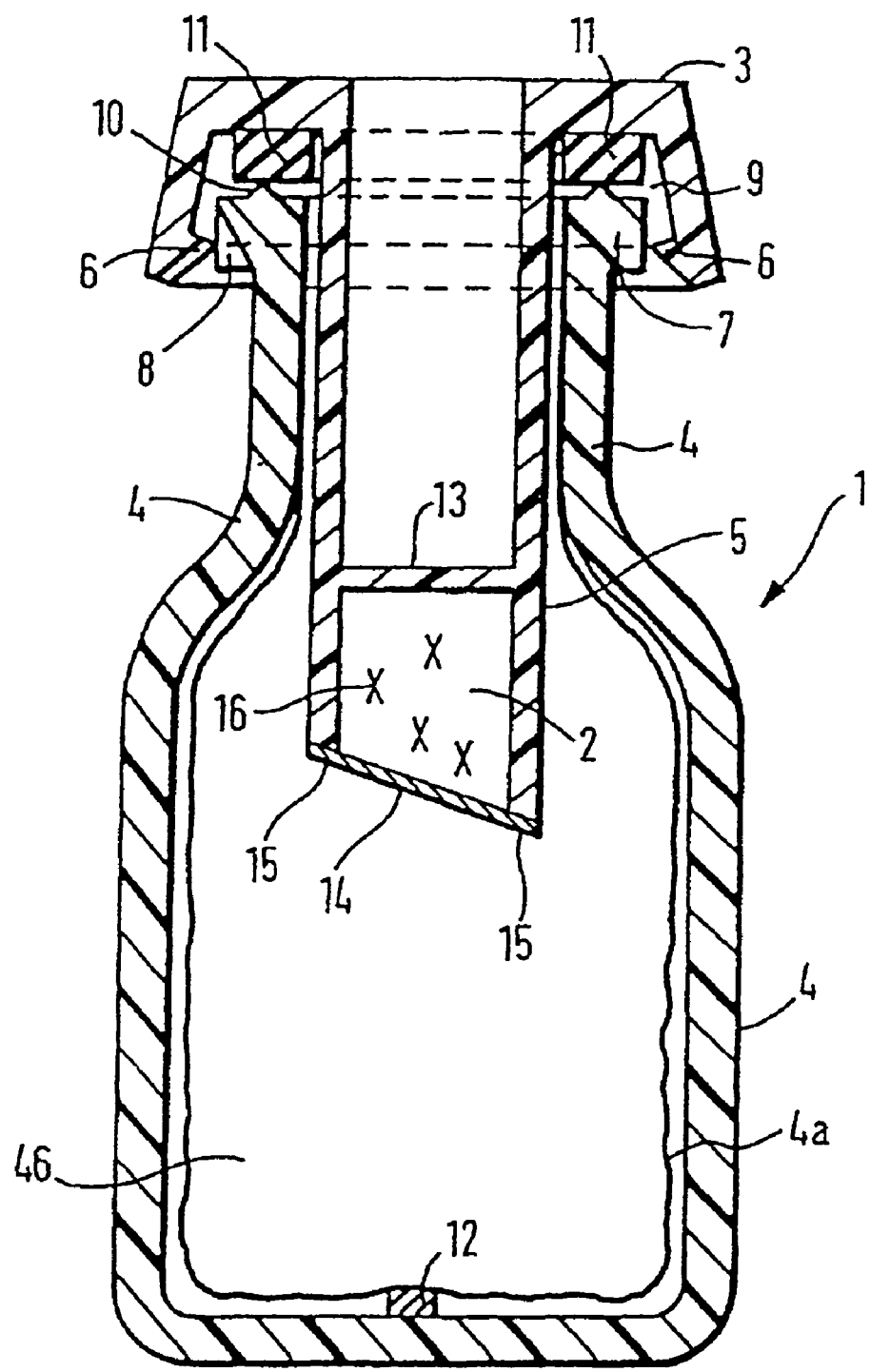
Figure 2:
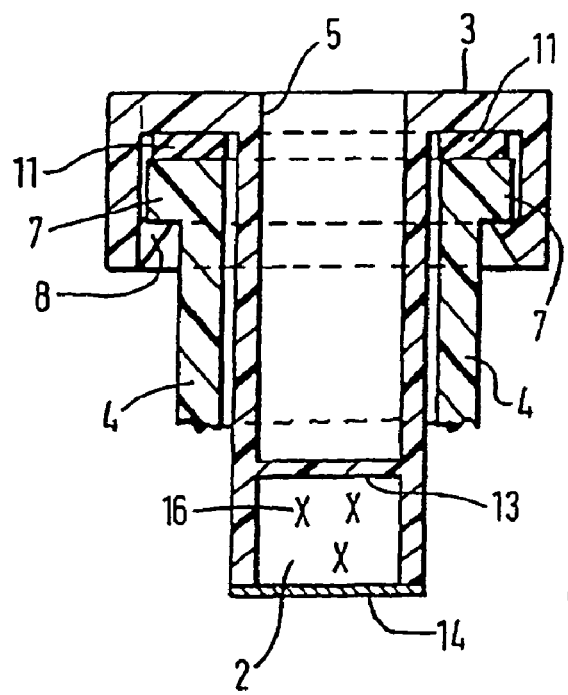
Figure 2A:
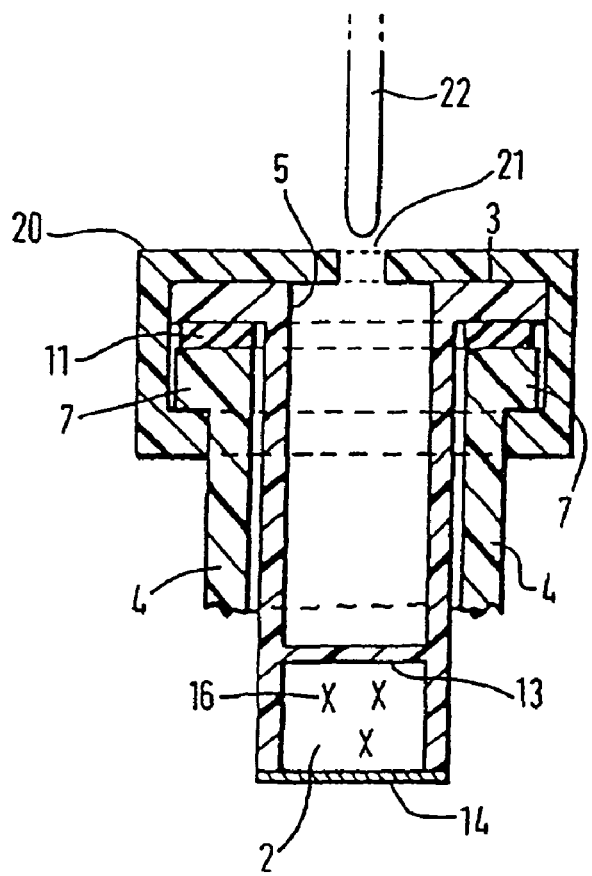
Figure 3A:
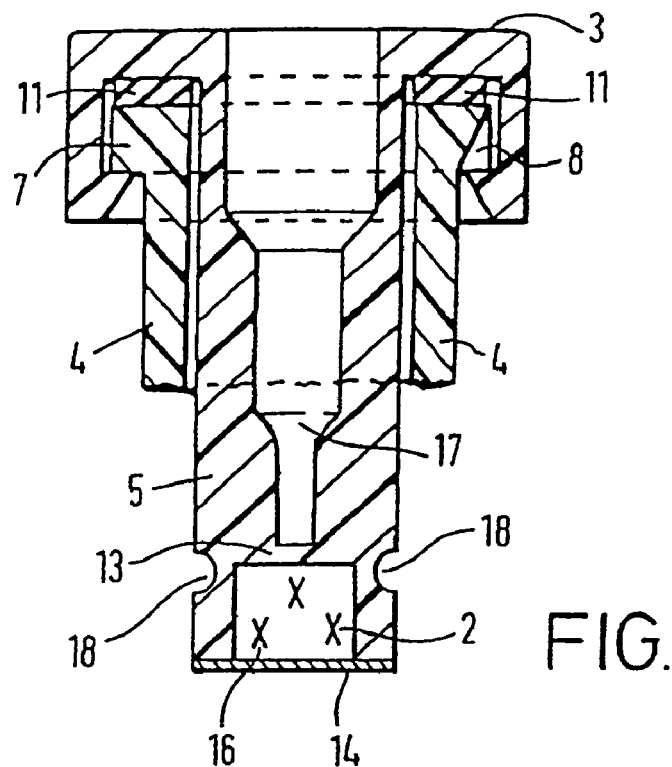
FIGS. 3b, 3c show other embodiments regarding the construction of the immersed connector (5) and the guide (17) for the cannula for withdrawing the liquid.
Figure 3B:
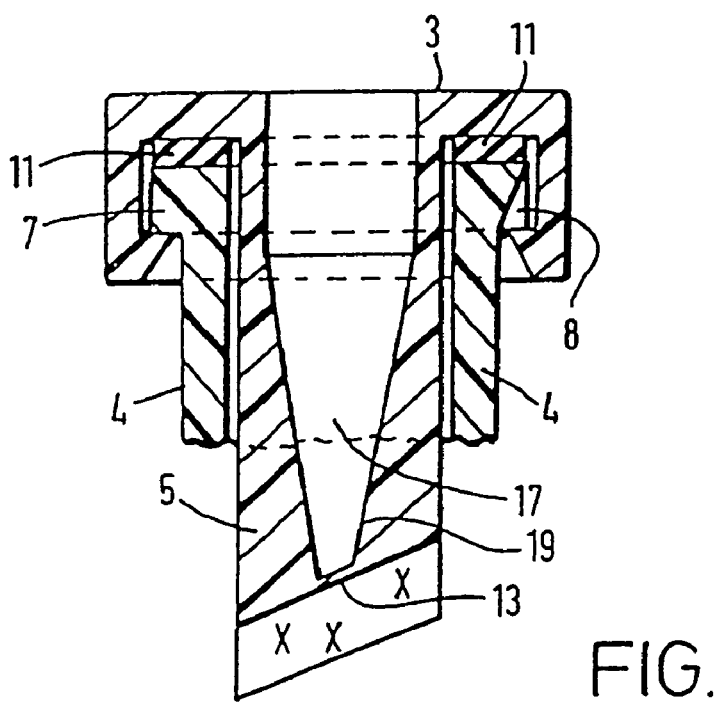
Figure 3C:
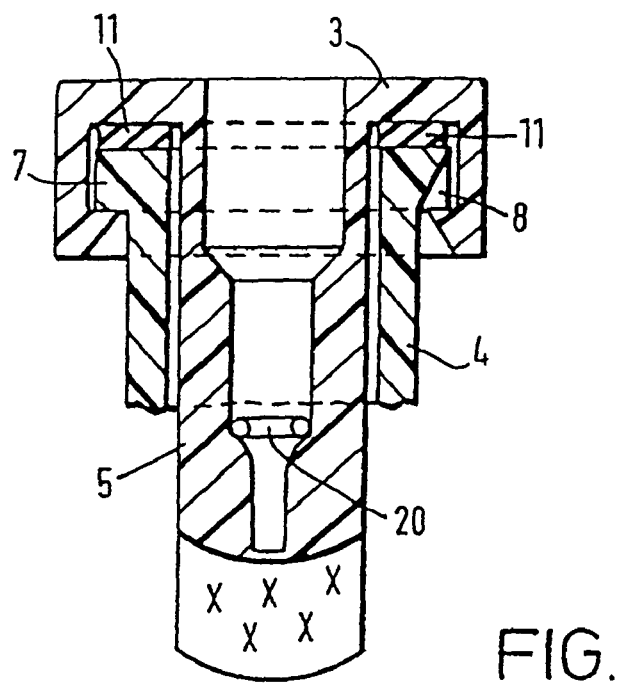

As shown in FIGS. 3b and 3c, the lower end of the immersed connector with the partition (14) may appropriately be chamfered, preferably by 20° to 60° relative to the axis of the connector. This makes it easier for the partition to be pierced with a "blunt" cannula the end face of which is perpendicular to the axis of the cannula. The advantages of a "blunt" as against a "sharp pointed" cannula are the small risk of injury to the user, the reduced machining work required to produce the end face of the cannula and the reduced risk of particle abrasion on the wall of the connector as the cannula is inserted.

Figure 4:
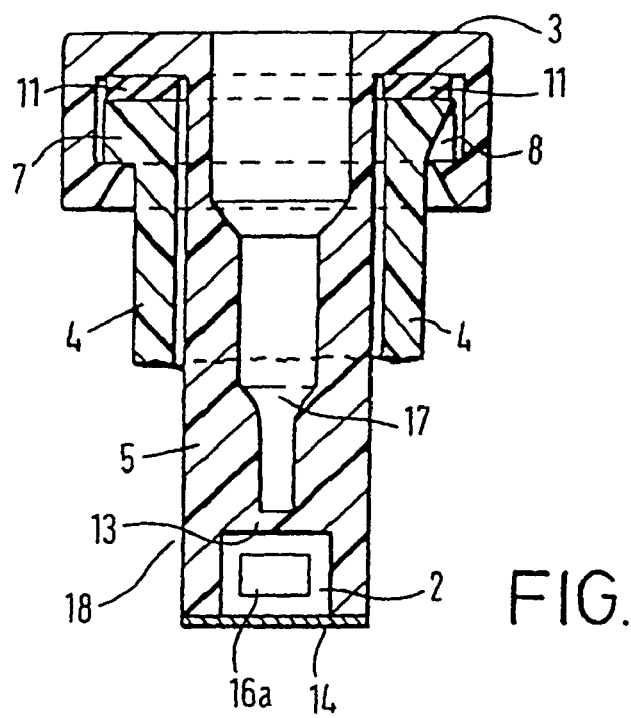

As shown in FIG. 4, which corresponds largely to FIG. 3a, the chamber (2) contains the active substance in the form of a small tablet. Compared with a powdered active substance, the active substance in the form of the minitablet according to the invention is substantially easier to introduce into the chamber (2), and also a tablet has advantages when the septum (13) is pierced by a cannula and subsequently the tablet (16a) is pushed through the foil (14). On the one hand, this ensures that the relatively hard tablet does not block the cannula, and on the other hand it ensures that the full amount of active substance from the chamber enters the container (4). With the highly effective drugs commonly used in metering aerosols nowadays, a precisely metered solution of active substance is absolutely necessary for purposes of drug safety. Moreover, if the chamber (2) is filled with a tablet, the sealing surface is not contaminated with dust, as would be the case if it were filled with powder.

The tablet in accordance with the invention has a diameter of between 2 and 3 mm, preferably between 2.2 and 2.3 mm, and is between 1.8 and 3.5 mm long. The tablet in accordance with the invention has a compressive strength of between 2 and 10 N/mm². The compressive strength is measured by clamping the tablet between flat surfaces and increasing the force until the tablet breaks up. The tablets were clamped in such a way as to come into contact with the flat surfaces along two generatrices (not with the top and bottom surfaces). The compressive strength is the force divided by the cross-sectional area (diameter times length of the cylindrical tablet).

The tablets in accordance with the invention consist of the active substance and conventional tableting excipients. Preferred active substances are those which can be used in low doses, e.g. up to 100 micrograms of active substance per single dose. These include, for example, atrovent, anticholinergics, β-sympaticomimetics, e.g. formoterol. The preferred excipients are lactose (200 mesh), glucose (200 mesh) and shape separating agents.

The container in accordance with the invention has a solvent volume of 4 ml, so that 0.5% solutions of active substance can be produced with a minitablet weighing 20 mg. The solvents are preferably water or ethanol or mixtures thereof. Other physiologically acceptable solvents are also suitable.

For removing liquid from the cartridge (1) in accordance with the invention, the partitions (13 and 14) are pierced with a cannula. Preferred embodiments are those wherein the container (4) has a readily deformable inner bag (4a) and the end of the cannula is located half way up the container when the liquid is drawn off. In this case, air bubbles have the least disruptive effect. Preferably, the minitablet (16a) in accordance with the invention is used as the supply of active substance.

The container and closure cap are generally made of plastics. Since the liquid packaged therein is virtually incompressible, the system of container and closure cap must be sufficiently deformable as the liquid expands in the warm. Similarly, when the liquid is drawn off, the walls of the container must yield or collapse sufficiently. The partition generally consists of a thin plastics film. Preferably, the partition (14) consists of a thin coated aluminum which is sealed.

Containers of this kind as well as the closure cap may be produced using the suitable plastics, e.g. polyethylene or preferably polypropylene, available to those skilled in the art.

The cartridge in accordance with the invention which is for drug formulations for an inhaler should have a long shelf life. For this reason it is necessary that the solvent cannot diffuse out of the interior (4b) of the container into the chamber (2) containing the active substance before use. In addition to having a sufficiently thick-walled chamber, an aluminum coating may also be applied to the outer or inner surfaces of the chamber (2). It should be emphasized that the insertion of the cartridge with the chamber (2) in the inhaler does not require any further manual strength on the part of the patient than the insertion of a conventional cartridge.

The invention claimed is:

1. A cartridge for propellant-free administration of a liquid pharmaceutical composition by inhalation, comprising:
   an elongate displacing device including an upper end and a lower end, the lower end for at least partial insertion into a container;
   a cartridge chamber disposed at the lower end of the displacing device and operable to store a pharmaceutical formulation, the cartridge chamber including at least one pierceably sealed opening;
   a cannula guide extending from the upper end of the displacing device to the cartridge chamber;
   a first pierceably sealed opening disposed between the cartridge chamber and the guide; and
   a second pierceably sealed opening disposed between the cartridge chamber and the container, which is sealed with a sealing film including one or more frangible points between the sealing film and a periphery of the second opening such that when the first opening is pierced by pressure, the sealing film tears at the one or more frangible points, wherein insertion of a cannula through the guide pierces the first pierceably sealed opening causing the second pierceably sealed opening to open and releases pharmaceutical formulation into a liquid solvent in the container to form the liquid pharmaceutical composition.

2. The cartridge of claim 1, wherein the displacing device is adapted to displace a portion of a solvent in the container when at least the lower end of the displacing device is inserted into the container.

3. The cartridge of claim 1, wherein first opening is sealed by a septum and the second opening is sealed with a sealing film.

4. The cartridge of claim 3, wherein the septum is made from a resilient material such that after piercing by the cannula, it is sealed off.

5. The cartridge of claim 1, wherein a lower end of the displacing device is chamfered.

6. The cartridge of claim 5, wherein the chamfering of the displacing device is between about 20° to its vertical axis.

7. The cartridge of claim 1, wherein the active, pharmaceutical substance is in one of dry form and liquid form.

8. The cartridge of claim 7, wherein the active pharmaceutical substance is in the form of a tablet.

9. The cartridge of claim 8, wherein the tablet is between 2 and 3 mm in diameter and between 1.0 and 4.0 mm long.

10. The cartridge of claim 8, wherein the tablet has a hardness of between 2 and 10 $N/mm^2$.

* * * * *